United States Patent [19]

Tsuji

[11] Patent Number: 5,220,198
[45] Date of Patent: Jun. 15, 1993

[54] SOLID STATE IMAGING APPARATUS IN WHICH A SOLID STATE IMAGING DEVICE CHIP AND SUBSTRATE ARE FACE-BONDED WITH EACH OTHER

[75] Inventor: Kiyoshi Tsuji, Tokyo, Japan

[73] Assignee: Olympus Optical Co., Ltd., Tokyo, Japan

[21] Appl. No.: 693,262

[22] Filed: Apr. 29, 1991

[30] Foreign Application Priority Data

Aug. 27, 1990 [JP] Japan .................. 2-225562
Apr. 10, 1991 [JP] Japan .................. 3-77964

[51] Int. Cl.⁵ .......................... H01L 23/12
[52] U.S. Cl. ........................ 257/731; 257/723; 257/680; 358/98
[58] Field of Search ........ 357/80, 75, 68, 74; 358/98, 213.26, 213.28; 128/4; 361/398

[56] References Cited

U.S. PATENT DOCUMENTS

| 4,777,524 | 10/1988 | Nakajimo et al. | 358/98 |
| 4,832,003 | 5/1989 | Yabe | 358/98 |
| 4,868,646 | 9/1989 | Tsuji | 358/98 |

FOREIGN PATENT DOCUMENTS 1-57660  3/1989  Japan ................. 358/98

*Primary Examiner*—Rolf Hille
*Assistant Examiner*—S. V. Clark
*Attorney, Agent, or Firm*—Armstrong, Westerman, Hattori, McLeland & Naughton

[57] ABSTRACT

A solid state imaging apparatus which can be made small in the contour is formed of a solid state imaging device chip provided with pad electrodes formed near a photoelectrically converting part, an interal connecting substrate bent so that a plurality of surfaces not on the same plane as this solid state imaging device chip may be formed and face-bonded and connected with the pad electrodes of this solid state imaging device chip through bumping members and electronic parts fitted on this connecting substrate and functionally connected to the solid state imaging device chip.

29 Claims, 13 Drawing Sheets

FIG.12
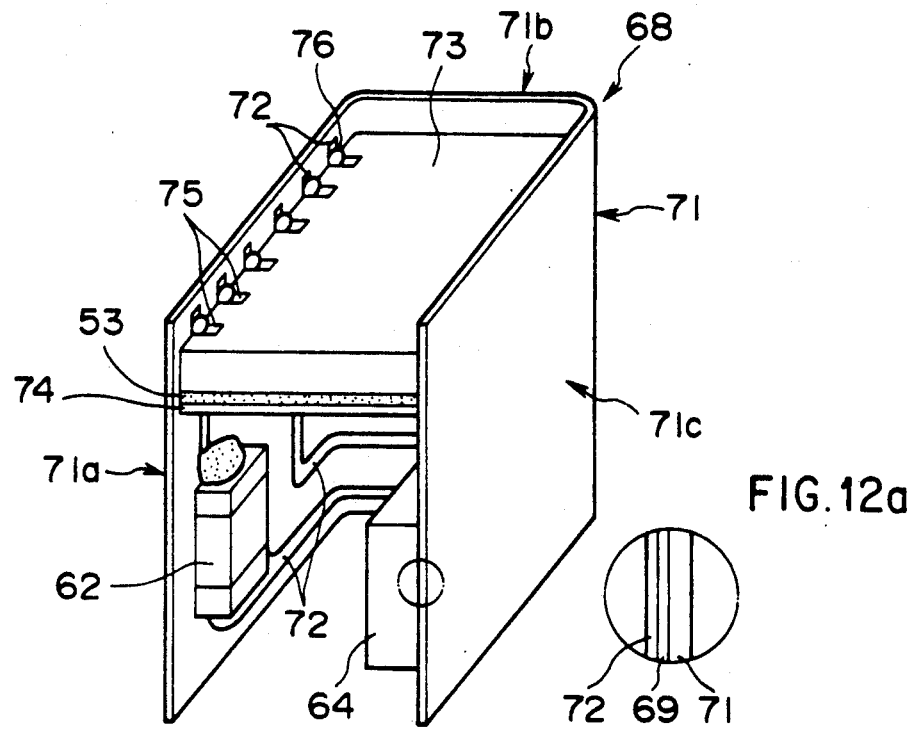
FIG.12a
FIG.13
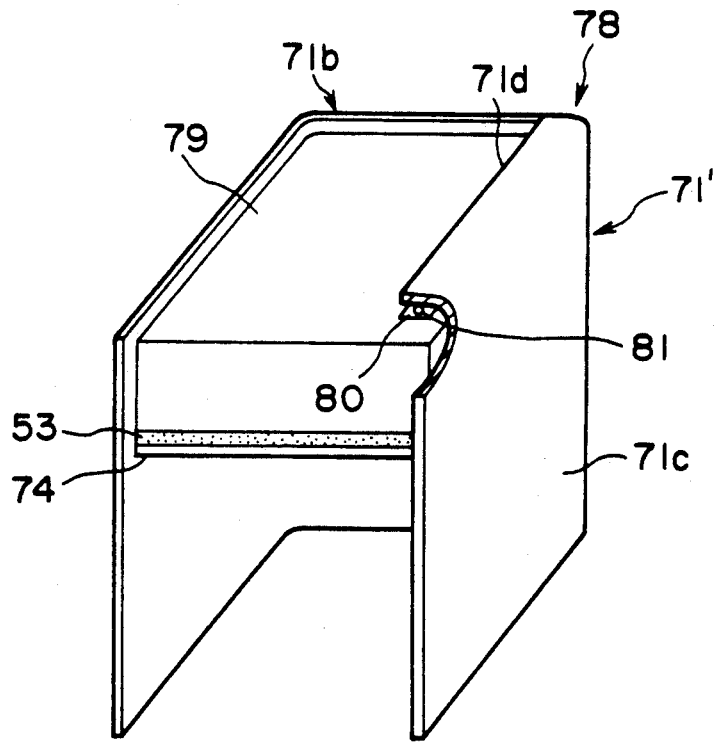

SOLID STATE IMAGING APPARATUS IN WHICH A SOLID STATE IMAGING DEVICE CHIP AND SUBSTRATE ARE FACE-BONDED WITH EACH OTHER

BACKGROUND OF THE INVENTION

1. Field of the Invention

This invention relates to a solid state imaging apparatus in which a solid state imaging device chip and substrate are face-bonded with each other.

2. Description of the Related Art

Recently, there is extensively utilized an endoscope whereby organs within a body cavity can be observed by inserting an elongate insertable section into the body cavity and various therapeutic treatments can be made by using, as required, a treating instrument inserted through a treating instrument channel. There is also used an electronic endoscope provided with a solid state imaging apparatus in the tip part of an insertable section.

In the endoscope, it is desirable that the insertable section is made small in diameter to reduce the pain or the like of the patient and therefore, in the above mentioned electronic endoscope, it is desirable that the solid state imaging apparatus provided in the tip part of the insertable section is also made small.

FIG. 1 shows an example of a solid state imaging apparatus of the prior art. This solid state imaging appartus has a CCD chip 101 as an image sensor. This CCD chip 101 is made of such semiconductor as silicon and is fitted in a package 102 made of ceramics. The above mentioned chip 101 is fixed by being die-bonded with a silver solder 104 or the like on a coval plate electrode 103 on the package 102 to give a reference potential to the chip 101. The above mentioned coval plate electrode 103 is connected to a part of a lead frame 105 within the package 102 so that the reference potential may be given through this lead frame 105. A bonding pad 106 for inputting and outputting with the outside a driving signal required for the CCD chip 101 and an output signal from the CCD chip 101 is provided on the CCD chip 101. This bonding pad 106 is conducted to a bonding pad 108 on the package 102 through a bonding wire 107. The bonding pad 108 on the package 102 is conducted to the lead frame 105 within the package 102. This lead frame 105 projects out as a signal terminal. The above mentioned CCD chip 101 is sealed air-tight with a face plate 109 made mostly of glass so as to be protected from humidity and dust.

In the case of a color chip CCD or the like, a color filter array 110 is pasted on the imaging surface of the CCD chip 101. This color filter array 110 is made by forming a color filter of a pixel density on glass and is pasted directly on the CCD chip 101 with an optical bonding agent in one case or is fixed to the package 102 by utilizing the step difference of the package 102 the same as in the illustrated face plate 109 in the other case.

Here, by using FIG. 2, there shall be explained the dimensions required for the bonding between the CCD chip 101 and package 102.

For example, the size of the bonding pad 106 on the CCD chip 101 side is 100 $\mu m \times 100$ $\mu m$ and its pitch is 150 to 200 $\mu m$. The distance l between the bonding pads 106 and 108 conducted by the bonding wire 107 is 0.7 to 1.0 mm, will be required to be 1.0 mm in the case of bonding by using an automatic bonding machine and will be 0.7 mm in the case of manually bonding. The flexing height h of the bonding wire 107 is 0.4 to 0.6 mm.

Here, in case the dimensions of the solid state imaging apparatus including the package 102 are to be reduced to the extreme, the dimensions required for the above mentioned distance l and height h, respectively, in the plane direction and height direction of the CCD chip 101 will be main factors. So long as the electric connection depends on the bonding wire 107, the contraction limit dimensions will be controlled by the above mentioned required dimensions of l and h.

In the publication of Japanese Patent Application Laid Open No. 67863/1987 is disclosed a technique of making only a solid state imaging apparatus small in a packaging state by making the material of the package a molded resin. However, as described above, the required dimensions by the wire bonding are not avoidable.

Here, the structure of an electronic endoscope provided with a solid state imaging apparatus in the tip part of an insertable section shall be considered. In the electronic endoscope, as it is desired to make the insertable section as small as possible in the diameter, the electronic parts fitted in the tip part are kept to a required minimum. The electric formation in the tip part including these electronic parts is as shown, for example, in the publication of Japanese Patent Applicatin Laid Open No. 209836/1987 and U.S. Pat. No. 4,868,646. The formation shall be explained by using FIG. 3.

Respective cables for a power source voltage VDD, earthing GND and driving signal are connected to a CCD chip 101. The CCD chip 101 requires various bias voltages in addition to the power source voltage. If it is intended to reduce the number of the cables to make the electronic endoscope small in the diameter, as shown in FIG. 3, it will be desirable to generate various bias voltages from the above mentioned power source voltage VDD with an IC 111 for generating various bias voltages. Because these various bias voltages differ in optimum value depending on the respective CCD chips 101, if formed as described above, the optimum voltage will be able to be generated in the tip part of the insertable section of each electronic endoscope and each electronic endoscopce may feed only the common power source voltage VDD, providing interchangeability.

Also, in the electronic endoscope, as shown in FIG. 3, there are required at least a bypass condenser 112 for stabilizing the power source voltage VDD in the tip part and a cable driving buffer IC 113 for cable-transmitting a CCD output signal.

Their connection with each other is as shown in FIG. 4. That is to say, the three of the CCD chip 101, a substrate 114 on which the electronic parts in the tip part are mounted and a scope cable 115 electrically connecting this substrate 114 with a signal processing apparatus outside the endoscope are tandem connected.

Such formation of a solid state imaging apparatus in the tip part of an insertable section as is shown in FIG. 5 is disclosed in the publication of Japanese Patent Application Laid Open No. 141788/1990. The CCD as a solid state imaging device is an interline transferring system which is the current trend today. In the case of a frame transferring system, the number of lines of driving pulses is larger than in the line transferring system and, if all the lines necessary to feed the above mentioned various bias voltages are combined, the number of terminals will be ten and several terminals. The array of two rows of CCD outside lead terminals 117 extended out of a package 102 fitted to the CCD chip 101 as shown in FIG. 5 is general and ideal. Therefore, the structure of the tip part of the insertable section of the electronic endoscope in which, as shown in FIG. 5, two of a first connected substrate 121 and a second connected substrate 122 are prepared for connected substrates to be connected to the package 102, the respective connected substrates 121 and 122 are connected by soldering 123 to the respective rows of the lead terminals 117 of the package 102 and further cables 115 are connected respectively to the connected substrates 121.

However, even in this case, in order to make the solid state imaging apparatus including the substrate smaller, there are two problems. The first problem is the waste space of soldering and connecting the outside lead terminals 117 and the first and second connected substrates 121, and 122 and the bad influence from heat generated by soldering The second problem is that the first connected substrate 121 and second connected substrate 122 are respectively independent, and therefore can be connected only with the CCD outside lead terminal 117 and cable 115, and can not give and take electric signals between them.

The cable 115 transmitting such signal not through the IC as the driving signal in FIG. 3 is conducted with the CCD chip 101 through the second connected substrate 122 and the signal group requiring the current source voltage and respective IC's 111 and 113 is given to the first connected substrate. In order to further reduce the substrate part, such electronic parts as the IC's 111 and 113 and condenser 112 should be fitted more efficiently to the first connected substrate 121 and second connected substrate 122 but as described above no electric signal can be given and taken between both connected substrates, therefore the electronic parts will deflect to one connected substrate 121 and the connected substrate 121 mounting the electronic parts necessarily lengthens.

In case it is considered to contract the tip part of the insertable section of the electronic endoscope to be small, the defects of the prior art will be summarized as follows:

One defect is the restriction of the dimensions in the direction (horizontal direction) parallel to the imaging surface in the wire bonding part between the solid state imaging device chip and package and the restriction of the dimensions in the direction (height direction) vertical to the imaging surface. The second defect is the bad condition caused by shortening in the lengthwise direction the connected substrate mounting the electronic parts between the solid state imaging device chip and scope cable.

Further, Japanese Patent Application Laid Open No. 50544/1986 discloses a solid state imging device fitted to a package and a flexible printed substrate connected to the back surface of this package. In this prior example, the solid state imaging device is not directly connected to the substrate, but rather through the package and therefore, the package is large.

On the other hand, the publication of Japanese Patent Application Laid Open No. 221719/1985 discloses that a through hole provided in a flexible printed substrate is present in an electrode of a solid state imaging device chip and solder is poured into the through hole to cause the electrode of the solid state imaging device chip and the printed substrate to conduct with each other. This prior art example is more adapted than the above described prior art example to make the tip part small. However, as the printed substrate is pulled out in the direction parallel to the imaging surface, the size in this direction will become large.

SUMMARY OF THE INVENTION

An object of the present invention is to provide a solid state imaging apparatus wherein the dimensions in the horizontal direction and vertical direction of a solid state imaging device chip can be made small and a substrate connected to the solid state imaging device chip can be made small.

Another object of the present invention is to Provide a solid state imaging apparatus whereby, particularly, in case it is provided in the tip part of an insertable section of an electronic endoscope, the tip Part of the insertable section can be made small.

The solid state imaging apparatus of the present invention comprises a solid state imaging device chip provided with a photoelectrically converting part formed on one side surface and having a photoelectrically converting function and pad electrodes formed near said photoelectrically converting part, an integral connecting substrate bent such that a plurality of surfaces not on the same plane as the above mentioned solid state imaging device chip may be formed and face-bonded and connected with the above mentioned pad electrodes of the above mentioned solid state imaging device chip through bumping members and electronic parts fitted on the above mentioned connected substrate and connected functionally to the above mentioned solid state imaging device chip so that the solid state imaging device chip and electronic parts may be fitted at a high density and the size may be made small.

BRIEF DESCRIPTION OF THE DRAWINGS

FIG. 1 is a sectioned view of a solid state imaging apparatus.

FIG. 2 is an explanatory view for explaining the dimensions necessary for bonding between a CCD chip and package in the solid state imaging apparatus in FIG. 1.

FIG. 3 is a block diagram showing an electrical formation in the tip part of an electronic endoscope.

FIG. 4 is an explanatory diagram showing the arrangement of a CCD chip, substrate and cables.

FIG. 5 is a sectioned view of a solid state imaging apparatus provided in the tip part of an electronic endoscope FIGS. 6 to 11 relate to the first embodiment of the present invention.

FIG. 12 is a perspective view of a solid state imaging apparatus of the second embodiment of the present invention.

FIG. 13 is a perspective view of a solid state imaging apparatus of the third embodiment of the present invention.

FIG. 19 is a sectional view showing the structure of the tip part of an electronic endoscope having the solid state imaging apparatus of the sixth embodiment built-in.

DETAILED DESCRIPTION OF THE PREFERRED EMBODIMENTS

Figure 9:
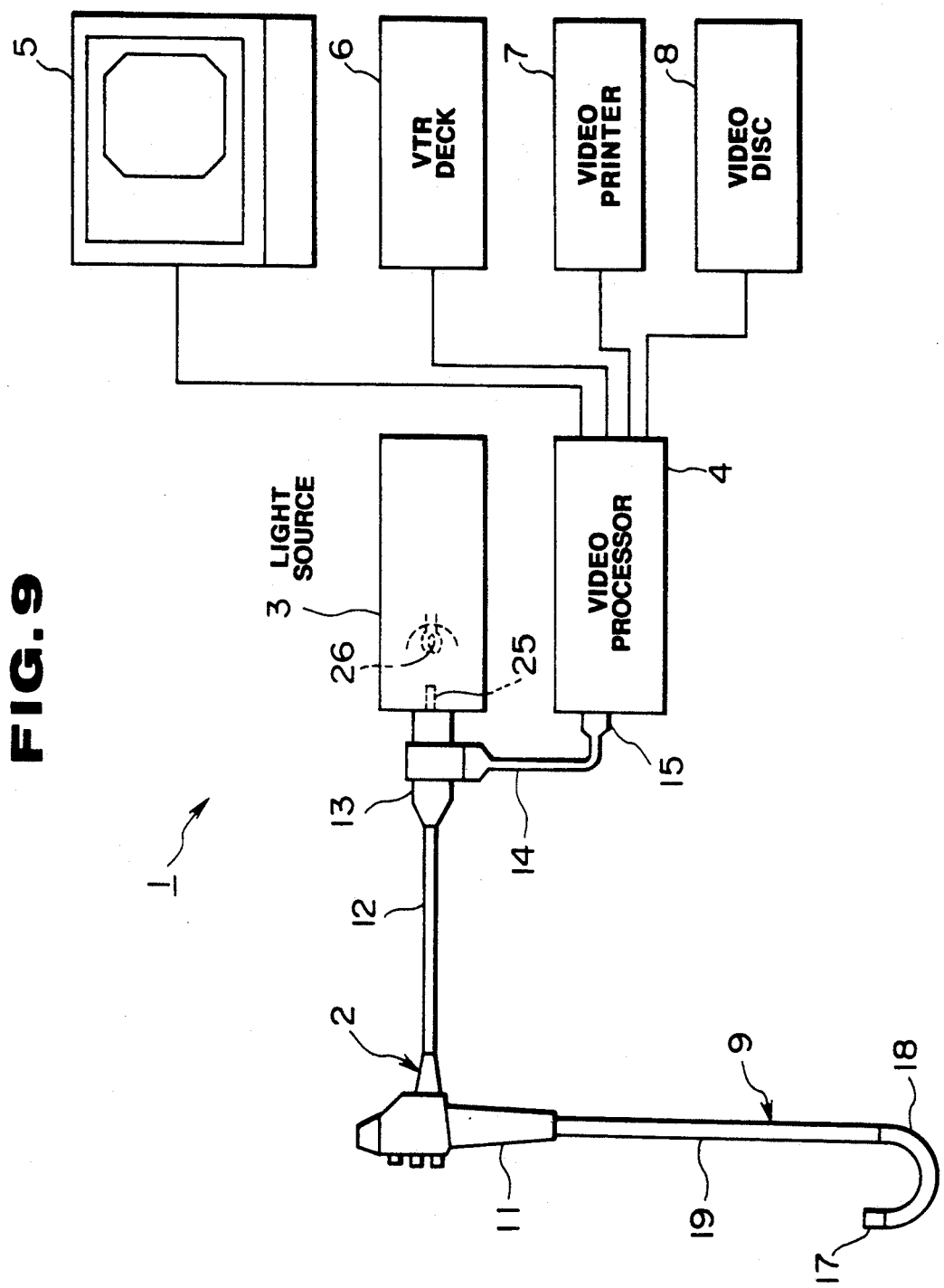
FIG. 9 is an explanatory diagram showing the whole of an endoscope system.

As shown in FIG. 9, an electronic endoscope system 1 comprises an electronic endoscope 2 having an imaging means built-in, a light source apparatus 3 feeding an illuminating light to this electronic endoscope 2, a video processor 4 processing signals for the imaging means, a monitor 5 displaying video signals output from this video processor, a VTR deck 6 recording moving pictures, a video printer 7 for printing out and a video disc 8 recording still pictures.

The above mentioned electronic endoscope 2 is provided with an elongate flexible insertable section 9 and a thick operating section 11 connected to this insertable section 9 at the rear end. A flexible universal cord 12 is extended sidewise from the above mentioned operating section 11 and is provided at the end with a connector 13 to be connected to the light source apparatus 3. A signal cord 14 is extended out of the above mentioned connector 13 and is provided at the end with a connector 15 to be connected to the video processor 4 to which are to be connected the monitor 5, VTR deck 6, video printer 7 and video disc 8.

The above mentioned insertable section 2 consists of a rigid tip part 17, curvable part 18 and flexible tube 19 in the order from the tip side.

Figure 8:
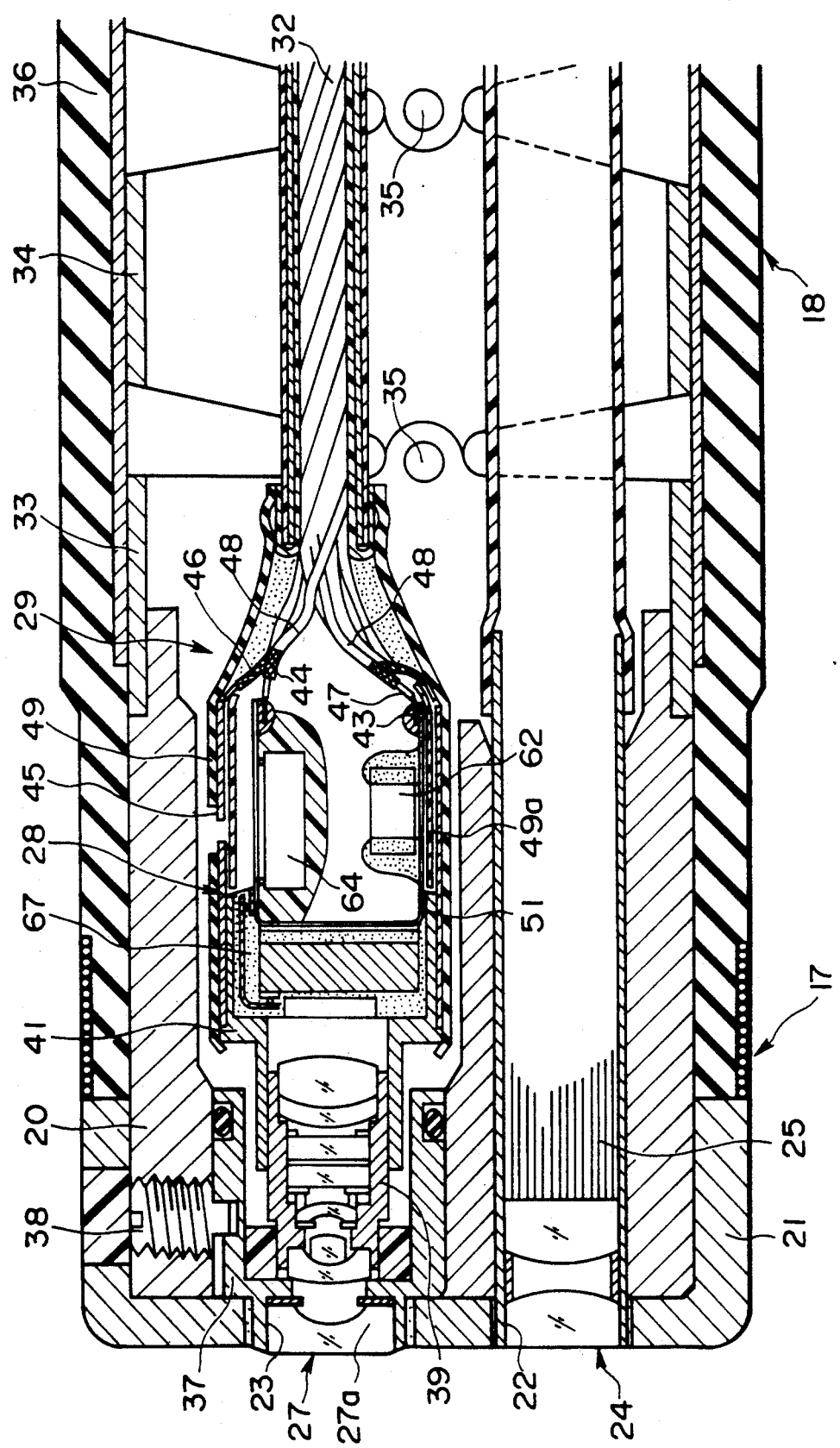
FIG. 8 is a sectional view of the tip side of an insertable section of an endoscope.

As shown in FIG. 8, the above mentioned tip part 17 has a rigid tip forming member 20 to which is fitted a tip cover 21. The tip forming member 20 and the tip cover 21 are provided with an illuminating window 22, observing window 23 and air and water feeding port and forceps channel port, not illustrated.

A light distributing lens system 24 is fitted inside the above mentioned illuminating window 22 and has a light guide 25 consisting of a fiber bundle connected at the rear end. This light guide 25 is inserted through the insertable section 9, operating section 11 and universal cord 12 and is connected to the connector 13. When an illuminating light emitted from a light source lamp 26 within the above mentioned light source apparatus 3 is incident upon the entrance end of this light guide 25, this illuminating light will be transmitted through the light guide and will be emitted forward from the tip surface further through the light distributing lens system 24.

Also, an imaging part 29 having an objective optical system 27 and a solid state imaging apparatus 28 of the first embodiment is provided inside the above mentioned observing window 23. A signal line 32 connected to this solid state imaging apparatus 28 is inserted through the insertable section 9, operating section 11, universal cord 12, connector 13 and signal cord 14 and is connected to the connector 15. This solid state imaging apparatus 28 is driven by the video processor 4 connected through the above mentioned connector 15 and the output signal of this solid state imaging apparatus 28 is processed to be a video signal by this video processor 4. The video signal from this video processor 4 is input into the above mentioned monitor 5, VTR deck 6, video printer 7 and video disc 8.

An air and water feeding tube not illustrated is connected to the above mentioned air and water feeding port, is inserted through the insertable section 9, operating section 11 and universal cord 12 and is connected to the connector 13. A forceps channel tube is connected to the above mentioned forceps channel port through a channel connecting pipe not illustrated, is inserted through the insertable section 9 and is connected to a forceps inserting port, not illustrated, provided in the operating section.

The above mentioned curvable part 18 has a curvable tube formed by connecting many substantially cylindrical articulate frames 33, 34, so as to be rotatable around articulation shafts 35 and covered on the outer peripheral part with a curvable rubber 36. A flexible tube 19 is connected to the last end articulate frame at the rear end.

For example, four angle wires (not illustrated) for the curving operation are inserted through the above mentioned insertable section 9 and are fixed at the tips to the foremost articulate frame 33 with guide wires not illustrated. Wire receptacles (not illustrated) are provided at predetermined intervals on the inner peripheral parts of the articulate frames 34 second and after from the tip side and the above mentioned angle wires are inserted respectively through the wire receptacles and are pushed and pulled by the rotation of an angle operating knob provided on the operating section 11 so that the curvable part 18 may be thereby curved in the vertical/horizontal direction.

The above mentioned imaging part 29 shall be explained more particularly in the following.

A first lens frame 37 is fixed with an imaging part fixing screw 38 in an observing through hole formed in the above mentioned tip forming member 20 and tip cover 21 and is fitted with an objective front lens 27a forming the objective optical system 27. A second lens frame 39 is fixed inside this first lens frame 37. The other lens system of the objective optical system 27 is fitted to this second lens frame 39. A device frame 41 is connected to this second lens frame 39 in the rear end part. The solid state imaging apparatus 28 is fixed to this device frame 41.

The signal line 32 is connected to the end of the U-like connected substrate 51 of this solid state imaging apparatus 28 and is a coaxial cable in which cable core wires 43 are connected to the above mentioned connected substrate 51 and shielding wires 44 are electrically connected to a shielding member 45 covering the above mentioned solid state imaging apparatus 28 by net wires (or a conductive bonding agent) 46. The above mentioned cable core wire 43 and shielding wire 44 are coated respectively with an insulating tube 47 and coating tube 48.

The outer periphery of the above mentioned shielding member 45 and the connecting part of the cable 32 are coated with an insulative thermoshrinkable tube 49. The connected substrate 51 in the rear of the part sealed with a resin 67 in the solid state imaging apparatus 28 is covered with an insulative thermoshrinkable tube 49a so as to be insulated.

Figure 1:
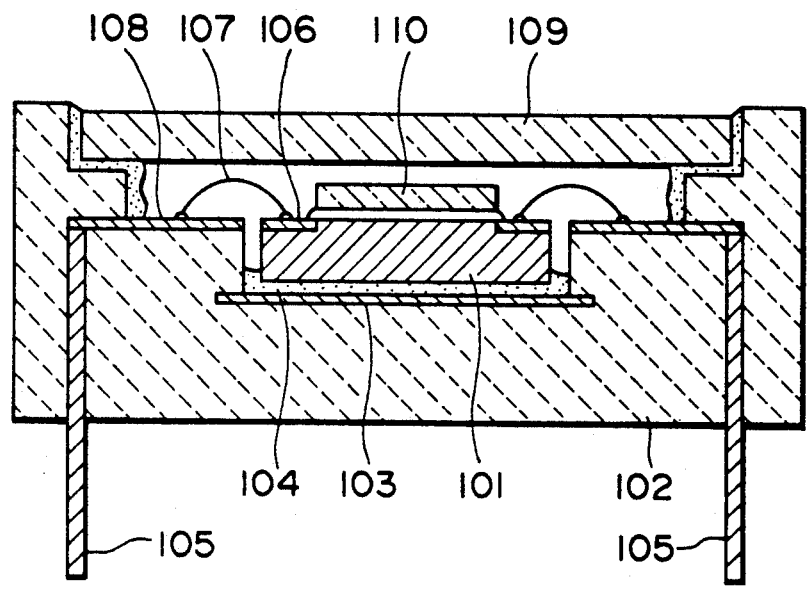
FIGS. 1 to 5 relate to prior art examples.
Figure 2:
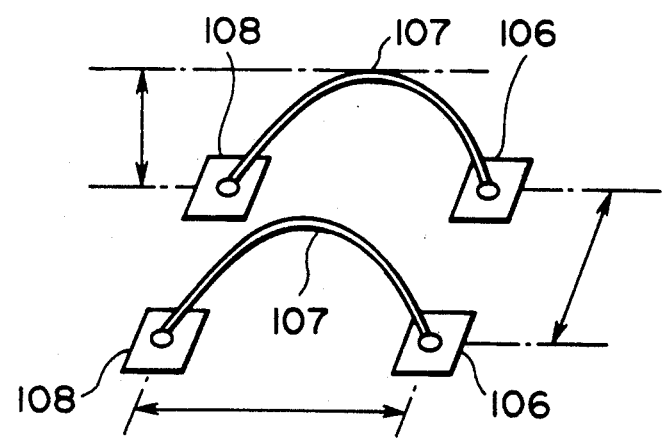
Figure 3:
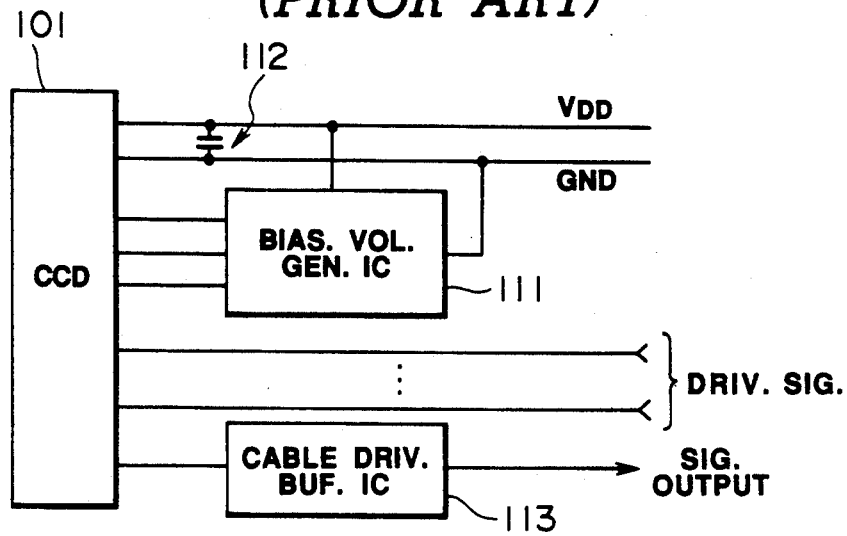
Figure 4:
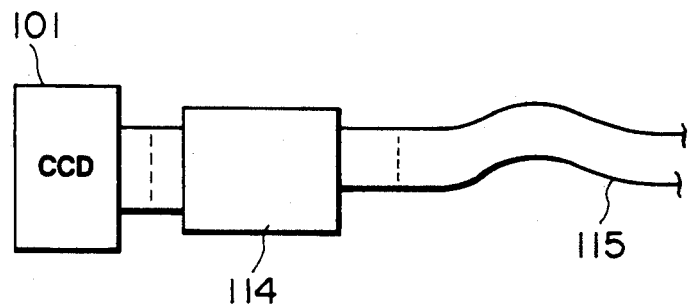
Figure 5:
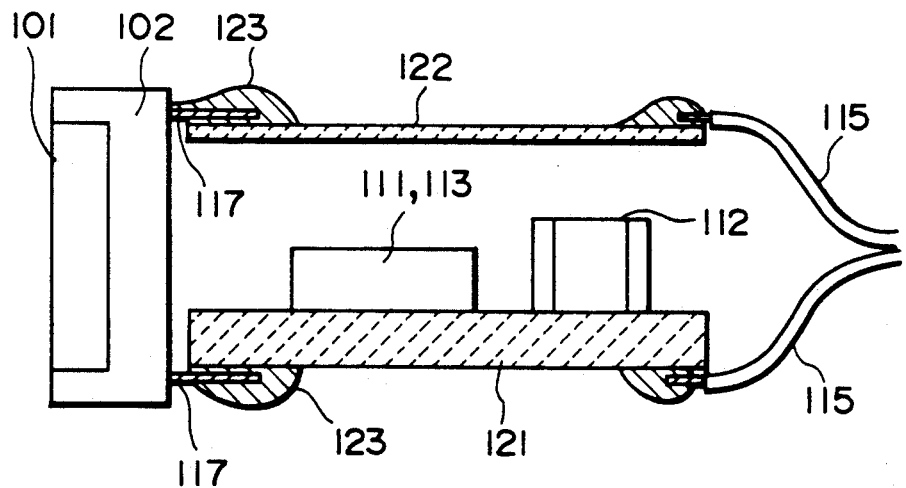
Figure 6:
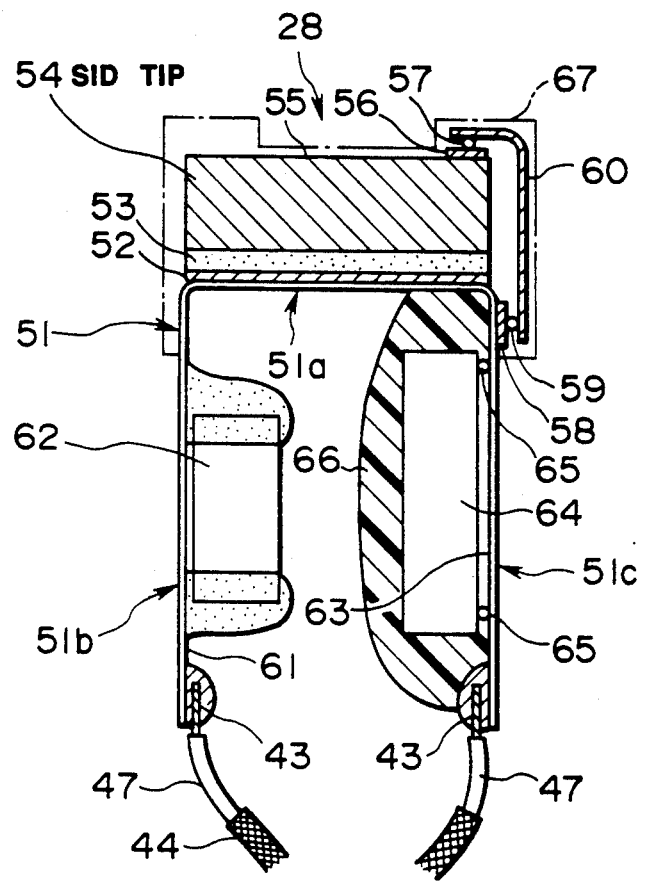
FIG. 6 is a sectional view of a solid state imaging apparatus.

The formation of the above mentioned solid state imaging apparatus 28 shall be explained in the following with reference to FIGS. 6 and 10.

The solid state imaging apparatus 28 has a connected substrate 51 consisting of a U-like bent flexible circuit substrate as an integral substrate bent to form a plurality of surfaces not on the same plane. This connected substrate 51 is formed of a central plane part 51a (mentioned as a central plane part hereinafter) and extended plane parts 51b and 51c extended out in the direction perpendicular to this central plane part 51a and is of a pattern structure on both surfaces. A die-bonding surface electrode 52 for a solid state imaging device chip (abbreviated as an SID chip) is formed on the outside surface of this central plane part 51a. A plate-shaped SID chip 54 is die-bonded with a silver solder 53 or the like on this die-bonding surface electrode 52 and is fed with a reference potential from the above mentioned die-bonding surface electrode 53.

Figure 10:
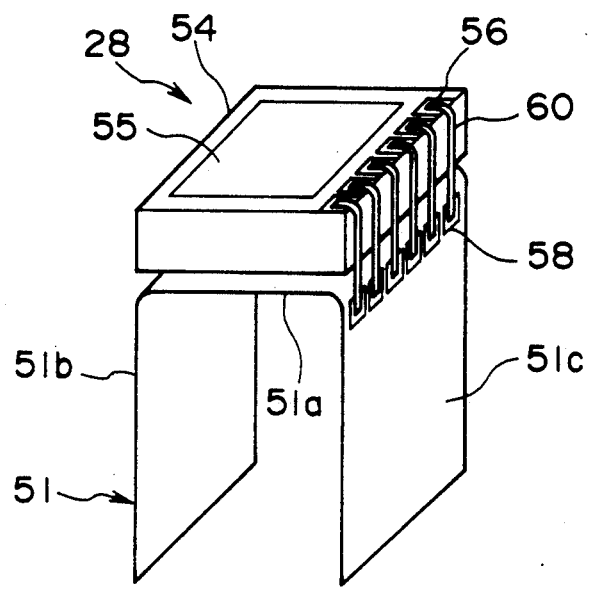
FIG. 10 is a perspective view of a solid state imaging apparatus.

A photoelectric converting part 55 (See FIG. 10 and pad electrodes 56 adjacent to this photoelectric converting part 55 and conducting with the above mentioned photoelectric converting part 55 are provided on one surface, that is, a light receiving surface of the above mentioned SID chip 54. Bumping members 57 made of gold or solder or conductive particles are provided on the respective pad electrodes 56. Bumping members 59 made of gold or solder or conductive particles are provided also on electrode patterns 58 of the extended plane part 51c in the positions corresponding to the above mentioned respective pad electrodes 56. The respective pad electrodes 56 and electrode patterns 58 are conductively connected by a lead frame 60 formed, for example, on a tape automated bonding (abbreviated as TAB hereinafter) film substrate through the above mentioned bumping members 57 and 59.

Also, the connected substrate 51 is bent like a U on the back surface side of the SID chip 54 to a space inside this U. The electronic parts are fitted within this space. For example, a condenser 62 as an electronic part functionally connected to the SID chip 54 is fitted, for example, by soldering on the inside surface (mentioned as the first surface hereinafter) 61 of one extended plane part 51b extended out in the thickness direction of the SID chip and is electrically connected to the electrode pattern. The tip part IC chip 64 as an electronic part functionally connected to the SID chip 54 is fitted by die-bonding, for example, through the bumping member 65 on the inside surface (mentioned as the second surface hereinafter) 63 of the other extended plane part 51c and is electrically connected to the electrode pattern. By the way, if the dimensions allow, the electric connection of the IC chip 64 with the electrode pattern may be by an ordinary wire bonding.

In either case, the IC chip is coated with an insulative sealing resin 66.

The above mentioned first surface 61 and second surface 63 are surfaces on the side opposite the SID chip die-bonding surface electrode 52 on the connected substrate 51. Therefore, on the surface on which the surface of the above mentioned lead frame 60 and the electrode pattern 58 are connected, no electronic part is fitted and therefore the lead frame 60 and electrode pattern 58 may be connected not only by the bumping member 59 but also by such ordinary method as soldering.

The SID chip 54 must be sealed the same as the above mentioned IC chip and is sealed with an insulative resin 67 (See FIG. 8. In FIG. 6, it is shown by the one-point chain line.) so that the respective sealed members may be protected by the resin 67. This resin 67 is transparent to pass light before the photoelectric converting part 55 but otherwise is made black to shield light.

The procedure of producing the solid state imaging apparatus 28 shall be explained in the following with reference to FIG. 7.

Figure 7:
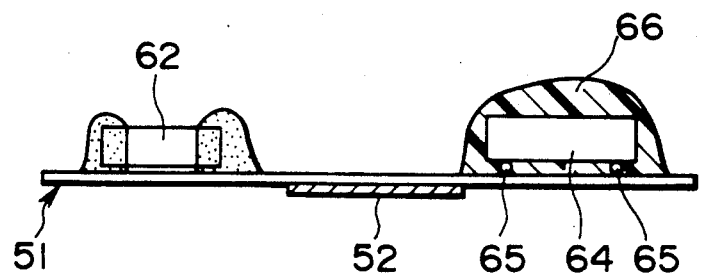
FIG. 7 is a sectional view showing electronic parts as fitted on connected substrate before bent.

At first, as shown in FIG. 7, in the connected substrate 51, the central plane part 51a and the extended plane parts 51b and 51c are made parallel, that is, in a flat plate state and, in this state, the condenser 62 and IC chip 64 are fitted and the SID chip 54 is die-bonded. Then, as shown in FIGS. 6 and 10, the above mentioned connected substrate 51 is bent. Then, by the lead frame 60 formed, for example, on the TAB film substrate, the pad electrode 57 of the SID chip 54 and the electrode pattern 58 on the connected substrate 51 are conducted and connected.

In case the above mentioned TAB film substrate is used, after the lead frame 60 is connected, only the film may be removed or the film may be left as it is.

Thus, in the solid state imaging apparatus 28 of this embodiment, the SID chip 54 is connected to the integral connected substrate 51 having a plurality of surfaces not on the same plane so that, when the SID chip 54 is made rectangular, in the positions corresponding to the two sides of the four sides, the extended plane parts 51b and 51c extended out in the direction vertical to the plane of the SID chip 54 will be arranged. The electronic parts are fitted on these extended plane parts 51b and 51c.

As the above mentioned extended plane parts 51b and 51c are formed by bending one original connected substrate signals can be received and given by the electrode pattern between them. Therefore, even in case the pad electrodes 56 on the SID chip 54 are arranged only on one side, the electronic parts will be able to be efficiently arranged by using both extended plane parts 51b and 51c and the connected substrate 51 will be able to be contracted. Also, a cable can be connected equally to both extended plane parts 51b and 51c.

Also, as the solid state imaging device chip 54 is mechanically and electrically connected directly to the connected substrate 51 through no package, the solid state imaging device chip 54 and connected substrate 51 can be connected at an extremely short distance and therefore the dimensions in the horizontal direction and vertical direction of the solid state imaging device chip 54 can be greatly contracted.

From the above, the dimensions in the diametral direction and lengthwise direction of the solid state imaging apparatus 28 provided in the tip part 17 of the insertable section 9 of the electronic endoscope 2 can be reduced. In the medical electronic endoscope which has recently come to be greatly used, the insertable section having the solid state imaging apparatus is inserted into the body cavity of the examinee and therefore the contraction of the dimensions in the diametral direction of the insertable section by the contraction in the diametral direction of the solid state imaging apparatus can contribute to the reduction of the pain at the time of the examination of the examinee.

The above mentioned endoscope 2 having the solid state imaging apparatus 28 including the connected substrate 51 and SID chip 54 is a non-bendable rigid part in the insertable section 9 and is bent in the cable part connected to this solid state imaging apparatus 28 so that the body cavity interior may be uniformly observed. According to this embodiment, the dimensions of the solid state imaging apparatus 28 particularly in the lengthwise direction of the insertable section can be greatly contracted, therefore the rigid part can be made shorter than before, the endoscope can be bent within a pipe cavity of a smaller diameter and thus the practical range in the observation can be greatly expanded.

Figure 11:
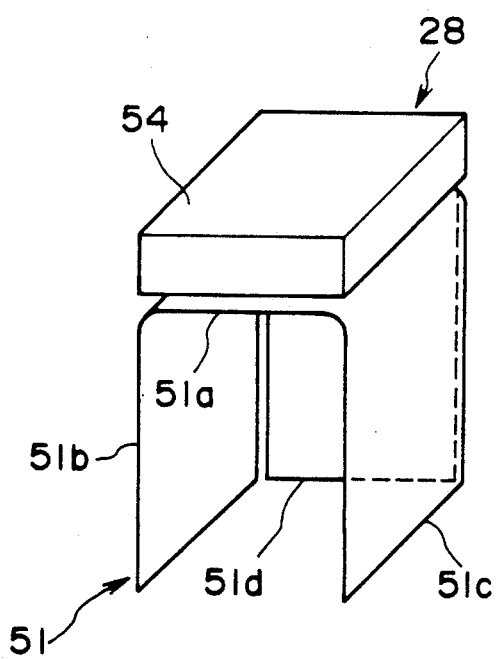
FIG. 11 is a perspective view of a solid state imaging apparatus of a modification of the first embodiment of the present invention.

In the positions corresponding to three or more sides of the four sides of the SID chip 54, the extended plane parts of the connected substrate 51 extended in the direction vertical to the plane of the SID chip 54 may be arranged. FIG. 11 shows an example that a T-like connected substrate 51 as an original form is bent to form a central plane part 51a and three extended plane parts 51b, 51c and 51a. The SID chip 54 is connected to the above mentioned central plane part 51a. According to this example, the electronic parts can be fitted to the three extended plane parts 51b, 51c and 51d and the freedom of fitting the electronic parts is larger than in the first embodiment.

The solid state imaging apparatus of the second embodiment of the present invention shall be explained in the following with reference to the perspective views in FIG. 12.

In a solid state imaging apparatus 68 of this embodiment, a metallic connecting substrate 71 using such metal as aluminum is used instead of the connecting substrate 51 using a flexible substrate. This metallic connecting substrate 71 is integral and is bent to be like U so that three plane parts 71a, 71b and 71c may be formed. The inside surface of this metallic connecting substrate 71 is made by once applying an insulative coating layer 69 on the metal surface and further forming electrode patterns 72 on this coating layer 69. An SID chip 73 is arranged inside the three plane parts 71a, 71b and 71c of the above mentioned metallic connecting substrate 71 and on one end side of each plane part and is fixed on the three sides of the four sides so as to contact the inside surfaces of the respective plane parts. In this embodiment, as there is no jointing surface giving a reference potential on the back surface of the SID chip in the metallic connecting substrate 71, a die-bonding substrate 74 is provided separately from this metallic connecting substrate 71 and the SID chip 73 is die-bonded with a silver solder 53 or the like on this die-bonding substrate 74 and is conducted with the metallic connecting substrate 71 by using the surface electrode on the back surface of this die-bonding substrate 74. The pad electrode 75 of the SID chip 73 is conducted and connected to the electrode pattern 72 on the metallic connecting substrate 71, for example, by soldering 76. As the above mentioned pad electrode 75 and electrode pattern 72 are in contact at right angles with each other, if ultrasonic waves or laser beams are used, such minute soldering will be possible.

In proper positions on the inside surfaces of the three plane parts 71a, 71b and 71c, such electronic parts as the condenser 62 and tip part IC chip 64 are fitted and cables not illustrated are connected.

Although not illustrated, by a sealing resin or sealing plate, the SID chip 73 is sealed and protected on the light receiving surface side the same as in the first embodiment.

According to this embodiment, by using the metallic connecting substrate 71, the unit itself of the solid state imaging apparatus 68 can be made stronger than by using a flexible substrate and therefore it is not necessary later to reinforce or shield the unit.

The other formations, operations and effects are the same as in the first embodiment.

FIG. 13 is a perspective view of a solid state imaging apparatus 78 of the third embodiment of the Present invention.

In the solid state imaging apparatus 78 of this embodiment, in a metallic connecting substrate 71', as one plane part 71c of the metallic connecting substrate 71 shown in FIG. 12 is opposed to the end of the light receiving surface of the SID chip 79, an extended part 71d is formed to project from the ends of the other plane parts 71a and 71b. This extended part 71d is bent so as to be parallel with the plane of the SID chip 79 so that the electrode patterns formed on this extended part 71d and the pad electrodes 80 of the SID chip 79 may be directly conducted and connected with each other by bumping members 81.

In FIG. 13, the electrode patterns and electronic parts on the metallic connecting substrate 71', cables to be connected to the metallic connecting substrate 71' and SID chip 79 sealing member are not illustrated.

The other formations, operations and effects are the same as in the second embodiment.

A solid state imaging apparatus of the fourth embodiment shall be explained in the following with reference to FIG. 14.

This solid state imaging apparatus 83 is of the metallic connecting substrate 71 provided with no extended part 71d in the metallic connecting substrate 71' in FIG. 13, that is, of the same form as is shown in FIG. 12 and is represented by the same reference numeral 71. On the other hand, in the SID chip 84, pad electrodes 85 are formed on the side surface opposed to the upper end, for example, of the plane part 71c and are conducted through bumping members 86 with the electrode patterns formed through coating layers on the metallic connecting substrate 71.

Figure 14:
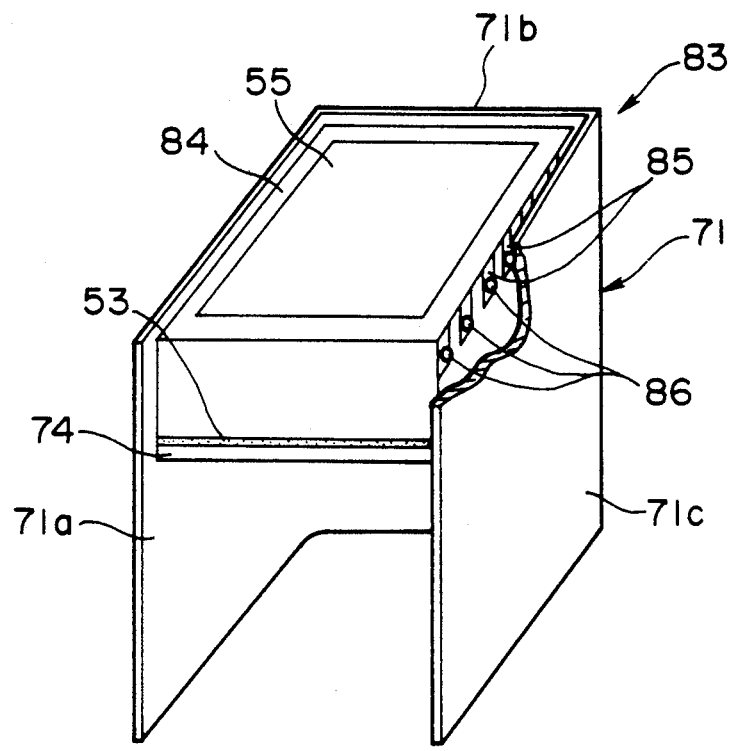
FIG. 14 is a perspective view of an essential part of a solid state imaging apparatus of the fourth embodiment of the present invention.
Figure 15:
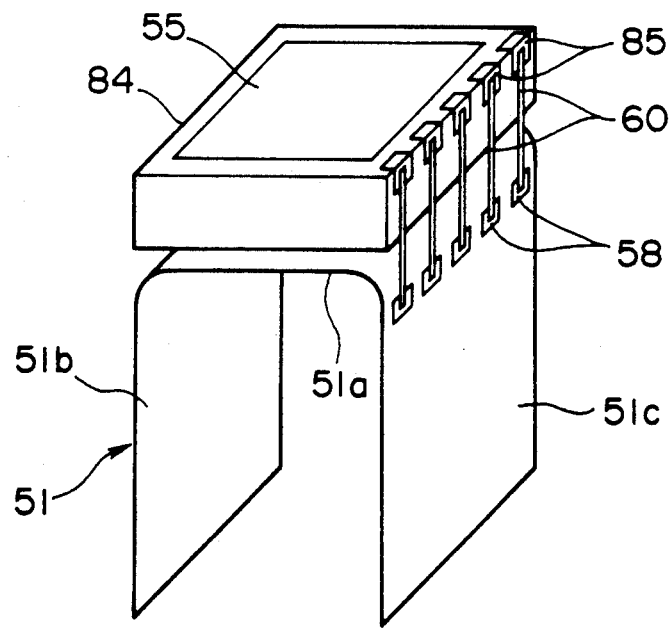
FIG. 15 is a perspective view of an essential part of a so id state imaging apparatus of a modification of the fourth embodiment of the present invention.

As shown in FIG. 14, the SID chip 84 having the pad electrodes 85 formed on the side surface may be formed as in the modification of the fourth embodiment shown in FIG. 15. On the back surface of this SID chip 84, the central plane part 51a of the connecting substrate 51 consisting of the flexible printed substrate in the first embodiment is secured with a silver solder or the like and the respective electrode patterns 58 formed near the boundary with the central plane part 51a in one extended plane part 51c are connected to the respective pad electrodes 85 through lead frames 60. By the way, as in the first embodiment, the respective electrode patterns 58 and the respective pad electrodes 85 may be connected with each other through the bumping members. As another modification, though not illustrated, there is considered a method wherein the pad electrodes 75 in FIG. 12 are formed on the back surface of the SID chip and the electrode patterns 72 of the extended part 71a are connected through a solder 76. In this case, the pad electrodes of the SID chip 73 may be formed on the side surface or back surface of this SID chip 73.

Figure 16:
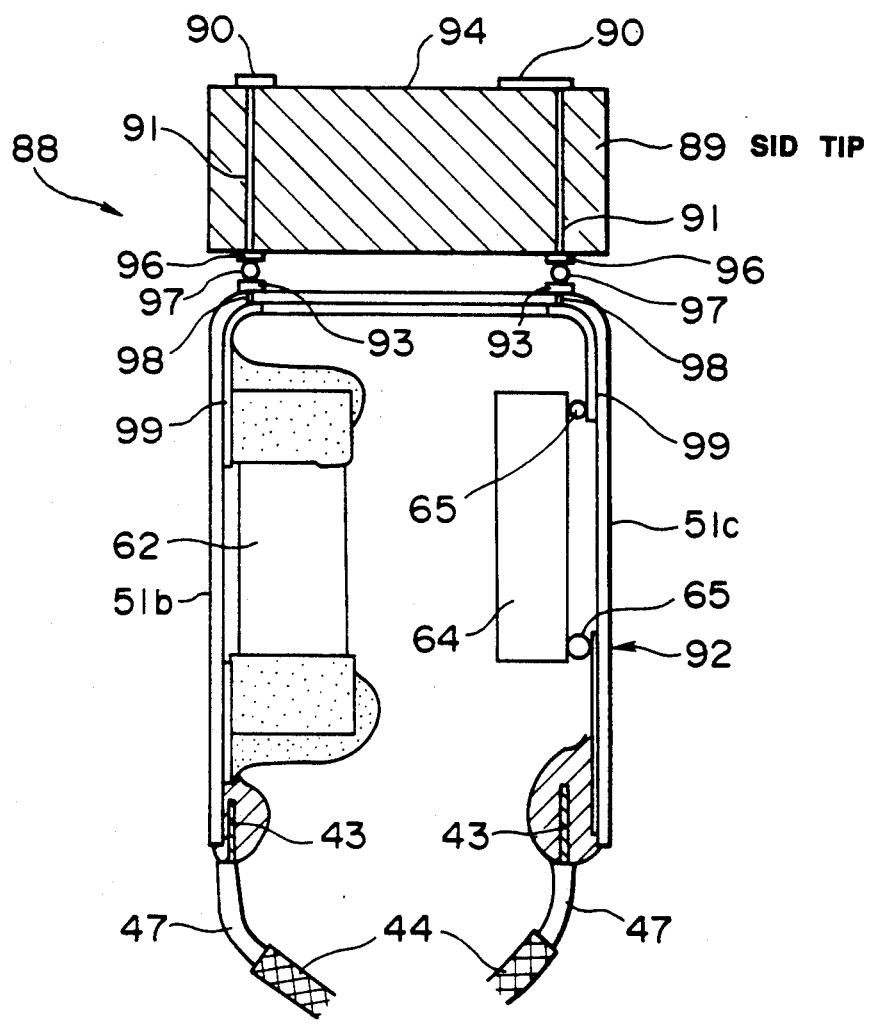
FIG. 16 is a sectional view of a solid state imaging of the fifth embodiment of the present invention.
Figure 17:
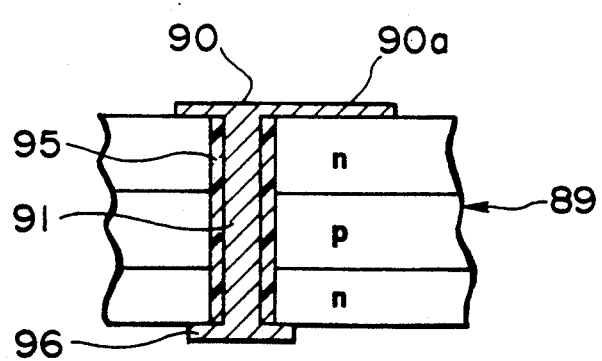
FIG. 17 is a sectional view showing a through hole within in the fifth embodiment.

FIG. 16 shows the fifth embodiment of the present invention. In the solid state imaging apparatus 88 of this embodiment, through holes 91 communicating with the respective pad electrodes 90 of the SID chip 89 are provided in the SID chip 89 so that the respective pad electrodes 90 and the electrode patterns 93 provided on the central plane part 92a of the connecting substrate 92 may be electrically connected with each other through the above mentioned through holes 91. On the light receiving surface of the SID chip 89, the pad electrodes 90 are formed respectively on both sides of the photoelectric converting part 94 and each pad electrode 90 is provided with a through hole 91 passing through the wafers of the SID chip 89 as shown in FIG. 17. Each through hole 91 is prevented by an insulator 95 from conducting with the channel structures of the outside wafers. The pad electrode 90 is connected with the photoelectrical converting part side through a pattern 90a.

In this embodiment, each pad electrode 90 on the light receiving surface conducts to a pad electrode 96 on the back surface through the through hole 91 and each pad electrode 96 further conducts with an electrode pattern 93 of the connecting substrate 92 through a bumping member 97. Also, each electrode pattern 93 conducts with an electrode pattern 99 on the first surface side of this connecting substrate 92 through a through hole 98 provided in the connecting substrate 92. The electrode patterns 99 on the first surface side are connected with the condenser 62 fitted on the plane extended part 92b of this connecting substrate 92 and with such electronic part as the IC 64 fitted on the other plane extended part 92c directly or through bumping members 65. The effects of this embodiment are substantially the same as in the first embodiment.

Figure 18:
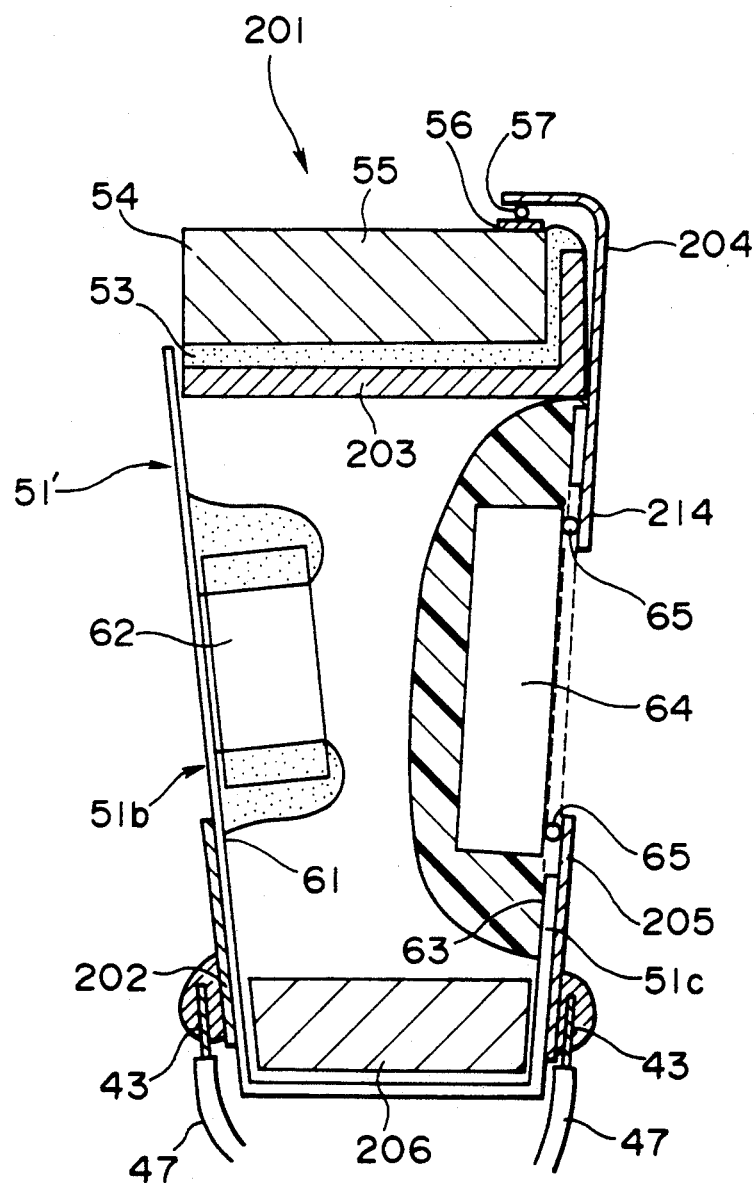
FIG. 18 is a sectional view of a solid state imaging apparatus of the sixth embodiment of the present invention.

FIG. 18 shows the sixth embodiment of the present invention. The connecting substrate 51' of the solid state imaging apparatus 201 is made like U consisting of a central plane Part 51a and two extended plane parts 51b and 51c extended in the direction substantially at right angles from both ends of it substantially the same as in the connecting substrate 51 of the first embodiment but the two extended plane parts 51b and 51c are fixed at the ends to the SID chip 54 side and the boundary end parts on the central plane Part 51a side are made the end of this connecting substrate 51' with electrode patterns 202 formed to be a cable connecting part.

Further, the connecting substrate 51' is tapered so that the distance between the end sides to be the cable connecting part sides, that is, the length (in the direction parallel with the light receiving surface) of the central plane part 51a in this case may be smaller than the distance between the SID chip 54 side ends in the two extended plane parts 51b and 51c. That is to say, the connecting substrate 51' is tapered so that the distance between the opposed extended plane parts 51b and 51c may be smaller toward the extended tip sides extended in the thickness direction from the SID chip 54.

In this embodiment, the SID chip 54 is fixed to a pedestal 203 formed of ceramics or glass for the reinforcement. Inner lead frames 204 are extended from the end of the extended plane part 51c and are connected at the tips to the pad electrodes 56 of the SID chip 54 through bumping members 57. (The inner lead frames 204 having only the leads projected on such bendable film substrate as of polyimide are connected instead of connecting the lead frames 60 as separate bodies as in the first embodiment.) Further, in this embodiment, the IC chip 64 fitted on the extended plane part 51c is connected by inner lead frames 205 extended on the inside of an opening somewhat larger than this IC chip 64 through bumping members 57.

Also, a fixing member 206 for bending this connecting substrate 51' is fitted inside the central plane part 51a.

In this embodiment, as the opposed extended plane parts 51b and 51c are tapered, the cable core wires 43 of the cables 47 can be connected as by soldering to the electrode patterns 202 provided on the respective second surfaces (outside surfaces) of the respective end parts on the central plane part 51a sides of the two extended plane parts 51b and 51c.

Figure 19:
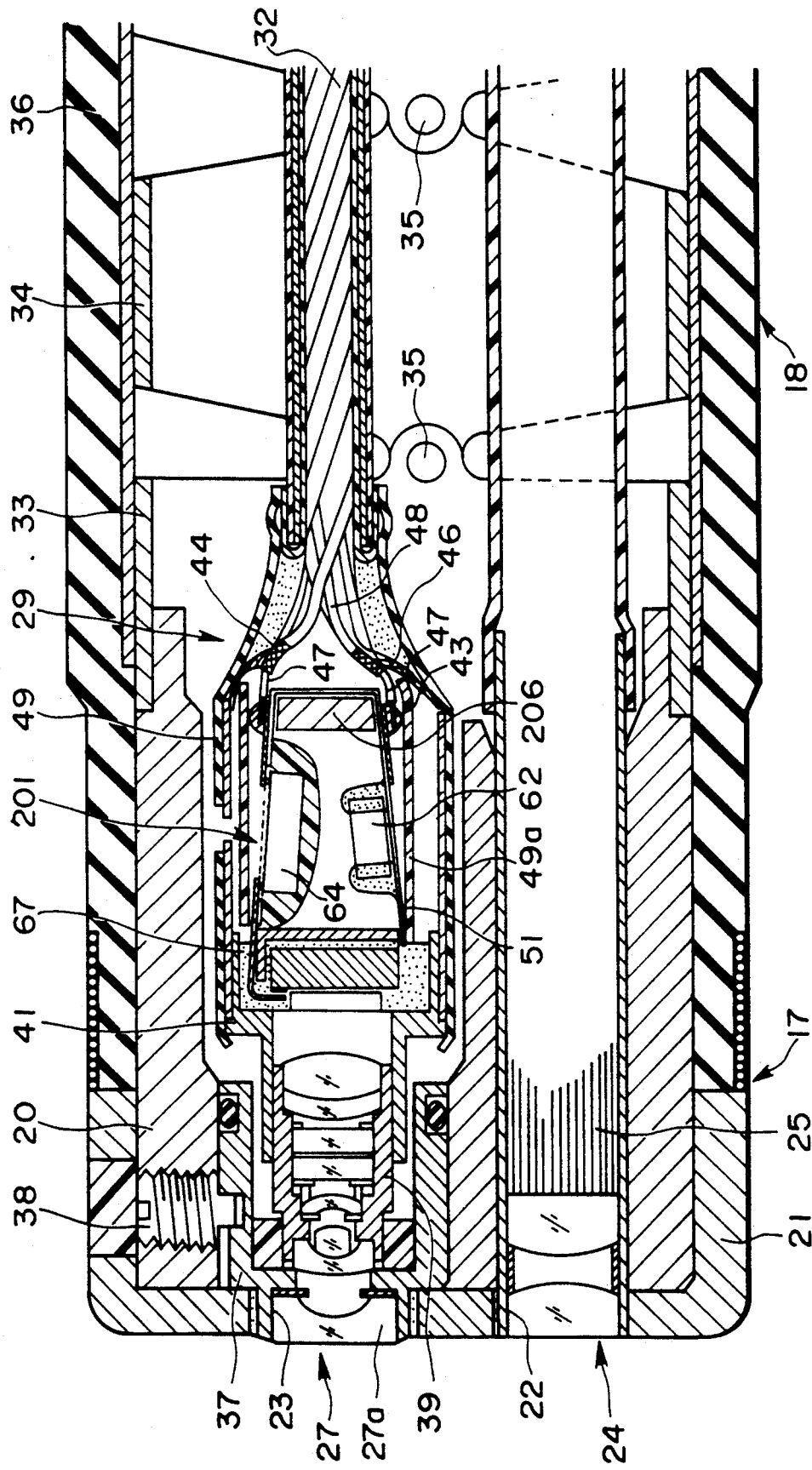

FIG. 19 shows this solid state imaging apparatus 201 as contained in the tip part 17 of the electronic endoscope 2. As understood from this drawing, in case the imaging part 29 is contained, as its contour is tapered to be smaller on the cable connecting part side, the foremost articulate frame 33 of the curvable part 18 will be able to be fixed more adjacently to the imaging part 29 side and, as a result, the length of the rigid part of the insertable section 9, that is, the distance from the tip of the tip part 17 to the rear end of the foremost articulate frame 33 can be made short.

The connecting substrate 51' and the pad electrodes 56 of the SID chip 54 may be connected with each other by a flexible substrate or the like without using the inner lead frames 205.

Figure 20:
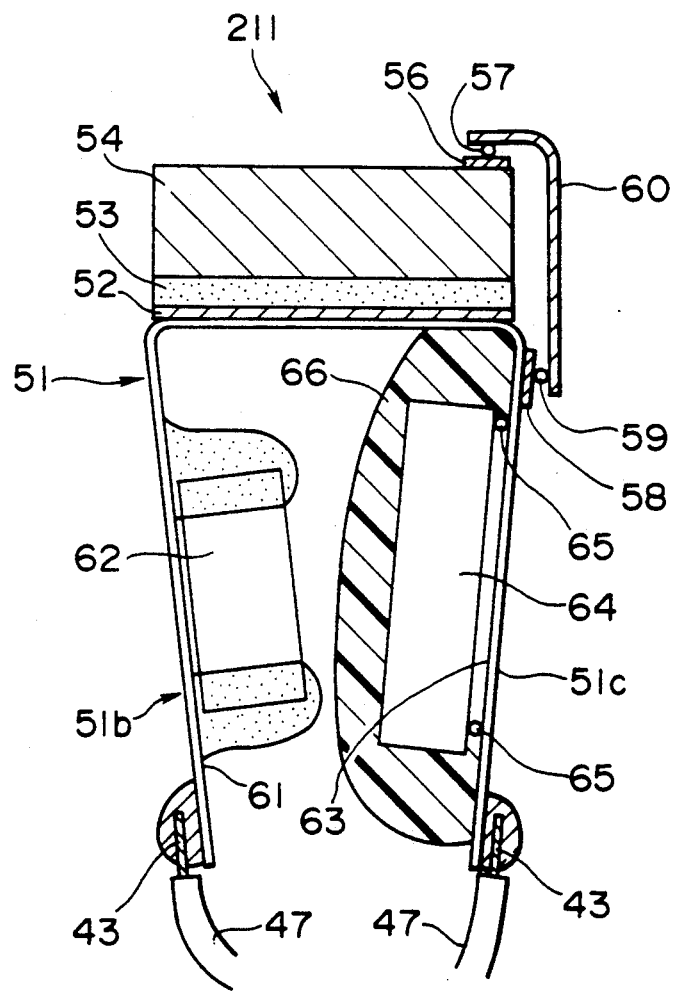
FIG. 20 is a sectional view of a solid state imaging apparatus of the seventh embodiment of the present invention.

FIG. 20 shows the seventh embodiment of the present invention. In the solid state imaging apparatus 211 of this embodiment, the distance between the two extended plane parts 51b and 51c of the U-like connecting substrate 51 is made narrower (smaller) on the end sides than the base end on the SID chip 54 side, for example, in the solid state imaging apparatus 28 of the first embodiment. That .is to say, the two extended plane parts 51b and 51c are extended and tapered in the direction of reducing the distance between their ends as displaced from the thickness direction at right angles with the central plane part 51a fixed to the SID chip 54 (so as to be tapered as in the sixth embodiment). The core wires 43 of the cables 48 can be connected as by soldering to the electrode patterns provided on the respective second surfaces (outside surfaces) at the ends of the two extended plane parts 51b and 51c.

Thus, as the distance between the two extended plane parts 51b and 51c connected with the cable core wires 43 of the cables 48 are made narrower on the end sides than on the SID chip 54 side, even if the cable core wires 43 are soldered on the outside surfaces on their end sides, the extended surface parts will not be protruded (in the direction parallel with the light receiving surface) at the ends from the base end by soldering, the work of connecting the cable core wires 43 will be easy and the contour dimensions will be able to be made small. The effects of this embodiment are substantially the same as in the sixth embodiment.

Figure 21A:
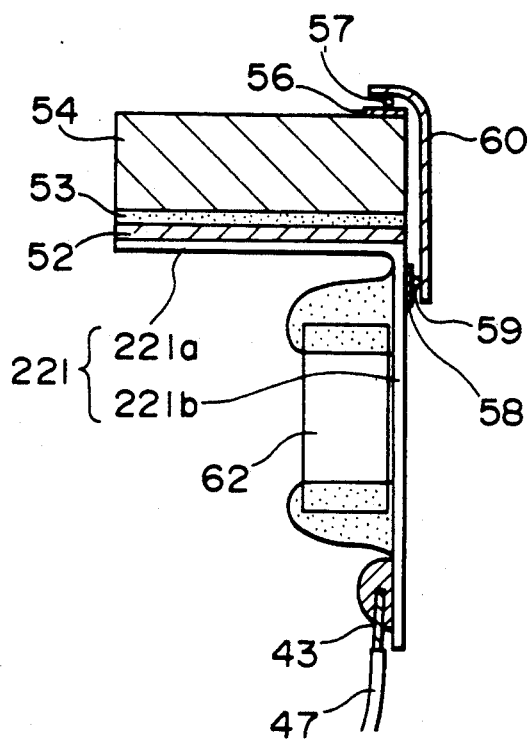
FIGS. 21a and 21b are side views showing parts of the eighth embodiment of the present invention.
Figure 21B:
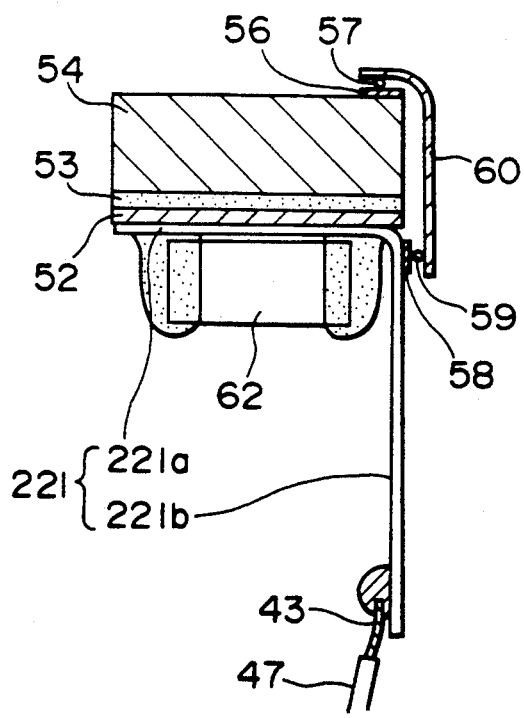

As shown, for example, in FIG. 21a, the connecting substrate 221 may be made like L consisting of the central plane part 221a and the extended plane part 221b extended in the direction intersecting at right angles with this central plane part 221a. In this case, such electronic part as, for example, the condenser 62 may be fitted on the extended plane part 221b or on the back surface of the central plane part 221a as shown in FIG. 21b, that is, on the surface on the side opposite the surface opposed to the SID chip 54.

Further, the present invention is not limited to the above mentioned respective embodiments. The connecting substrate may be formed like L having two surfaces intersecting at right angles with each other and the SID chip may be connected so that the two adjacent sides of the SID chip may contact the respective surfaces of this connecting substrate. Further, a different embodiment can be formed by partly combining the above described embodiments. These modifications belong also to the present invention.

The present invention can be applied not only to the electronic endoscope but also to various imaging apparatus.

What is claimed is:

1. A solid state imaging apparatus comprising:
a solid state imaging device chip provided on one surface of a connecting substrate, wherein said chip is provided with a photoelectrically converting part formed on one surface of said chip and having a photoelectrically converting function and pad electrodes formed near said photoelectrically converting part, wherein said connecting substrate is bent so that a plurality of surfaces not in the same plane as said solid state imaging device chip may be formed, wherein said plurality of surfaces are face-bonded to and connected with said pad electrodes of said solid state imaging device chip through bumping members; and
electronic parts fitted on said connecting substrate and connected functionally to said solid state imaging device chip.

2. A solid state imaging apparatus according to claim 1 wherein said pad electrodes are formed on the same plane as said photoelectrically converting part.

3. A solid state imaging apparatus according to claim 1 wherein said pad electrodes are formed on at least one side surface of said solid state imaging device chip.

4. A solid state imaging apparatus according to claim 1 wherein said connecting substrate is U shaped having a fixed substrate part in which one surface is mechanically fixed to the other surface of said solid state imaging device chip and to said plurality of surfaces having extended substrate parts bent in a direction substantially at right angles with said fixed substrate part on both sides of said fixed substrate part and extended, respectively, in a direction perpendicular to a plane containing said surface of said connecting substrate provided with said solid state imaging device chip.

5. A solid state imaging apparatus according to claim 4 wherein at least one of said extended substrate parts has electrodes formed in the part adjacent to said fixed substrate part and said electrodes have lead frames electrically connected to said pad electrodes through bumping members.

6. A solid state imaging apparatus according to claim 4 wherein at least one of said extended substrate parts has said electronic parts fitted on the surface opposed to the other of said extended substrate parts.

7. A solid state imaging apparatus according to claim 1 wherein said connecting substrate has a fixed substrate part mechanically fixed on one side to at least one side surface of said solid state imaging device chip, wherein said connecting substrate is extended in a direction perpendicular to a plane containing said surface of said connecting substrate provided with said solid state imaging device chip.

8. A solid state imaging apparatus according to claim 1 wherein said connecting substrate has a U-shaped substrate part in which respective ends of the U-shaped bend contact three sides of said solid state imaging device chip, and three side surfaces of said substrate are extended out in a direction perpendicular to a plane containing said surface of said connecting substrate provided with said solid state imaging device chip.

9. A solid state imaging apparatus according to claim 8, wherein an end of at least one surface forming said U-shaped substrate part is mechanically fixed to at least one said side surface.

10. A solid state imaging apparatus according to claim 8 wherein electrodes face-bonded and connected to said pad electrodes through bumping members are formed on said end of at least one surface forming said U-shaped substrate part.

11. A solid state imaging apparatus according to claim 8 wherein said U-like substrate part is fitted with said electronic parts on the inside surface enclosed with said U-like substrate part.

12. A solid state imaging apparatus according to claim 1 wherein said connecting substrate part has a fixed substrate part mechanically fixed on one end to the side surface of said solid state imaging device chip and extended out in a direction perpendicular to a plane containing said surface of said connecting substrate provided with said solid state imaging device chip and an extended substrate part provided with conductive pattern parts face-bonded and connected to said pad electrodes through said bumping members in said pad electrodes of said solid state imaging device chip.

13. A solid state imaging apparatus according to claim 1 wherein said connecting substrate part has lead frame parts face-bonded and connected at the ends on one side to said pad electrodes through said bumping members.

14. A solid state imaging apparatus according to claim 13 wherein said lead frame parts are extended out to said one surface side from said other surface side of said solid state imaging device chip along the side surface of said solid state imaging device chip and said lead frame parts are connected at the end on one side to said pad electrodes through said bumping members.

15. A solid state imaging apparatus according to claim 13 wherein said lead frame parts are connected to said pad electrodes in which said lead frame parts are formed at said ends on one side on the side surface of said solid state imaging device chip.

16. A solid state imaging apparatus according to claim 14 wherein said lead frame parts are connected to said pad electrodes in which said lead frame parts are formed at said ends on one side on the same plane as said photoelectrically converting part.

17. A solid state imaging apparatus according to claim 1 wherein said solid state imaging device chip has through hole parts formed in the thickness direction so as to conduct with said pad electrodes formed on said one surface and the pad electrodes formed on the other surface of said solid state imaging device chip.

18. A solid state imaging apparatus according to claim 17 wherein said through hole parts are electrically connected with the electrode parts formed on said connecting substrate having a surface opposed to said other surface of said solid state imaging device chip.

19. A solid state imaging apparatus according to claim 18 wherein said electrode parts conduct with conductive patterns formed on the back surface of the surface on which said electrode parts are formed through the through holes conducting to said electrode parts.

20. A solid state imaging apparatus according to claim 1 wherein said connecting substrate step is extended out in said thickness direction along at least one side surface of said solid state imaging device chip and has at one end lead frame parts conducting with said pad electrodes through said bumping members.

21. A solid state imaging apparatus according to claim 1 wherein said connecting substrate is a flexible substrate.

22. A solid state imaging apparatus according to claim 1 wherein said connecting substrate is mechanically connected with said solid state imaging device chip, has a surface extended out at least in the thickness direction of said solid state imaging device chip so as to form a space as opposed to the other surface of said solid state imaging device chip and has conductive patterns formed.

23. A solid state imaging apparatus according to claim 22 wherein said electronic parts are fitted on said connecting substrate so as to occupy said space.

24. A solid state imaging apparatus according to claim 1 wherein said bumping member is formed of gold, solder or conductive particles.

25. A solid state imaging apparatus according to claim 1 wherein said connecting substrate forms a plurality of surfaces for said solid state imaging device chip and said electroic parts are mounted on at least two surfaces of said plurality of surfaces.

26. A solid state imaging apparatus according to claim 1 wherein said connecting substrate is tapered in the thickness direction of said solid state imaging device chip so that said solid state imaging device chip may be thinner on the end side.

27. A solid state imaging apparatus according to claim 1 wherein said solid state imaging device chip is connected with a pedestal of ceramics or glass so as to be reinforced.

28. A solid state imaging apparatus according to claim 1 wherein said connecting substrate has a fixed substrate in which one surface is mechanically fixed to the other surface of said solid state imaging device chip and an extended substrate being in a direction substantially at right angles with said fixed substrate part from at least one end of said fixed substrate and extended respectively in a direction perpendicular to a plane containing said surface of said connecting substrate provided with said solid state imaging device chip.

29. A solid state imaging apparatus comprising:
a solid state imaging device chip provided on one surface of a connecting substrate, wherein said chip is provided with a photoelectrically converting part having a photoelectrically converting function on one surface of said chip and pad electrodes electrically connected with said photoelectrically converting part, wherein said connecting substrate is bent so that a imaging device chip may be formed, wherein said plurality of surfaces have inner lead frames face-bonded and connected with said pad electrodes of said solid state imaging device chip through bumping member; and
electronic parts fitted on said connecting substrate and connected functionally to said solid state imaging device chip.

* * * * *